United States Patent [19]

Brown

[11] Patent Number: 4,557,186
[45] Date of Patent: Dec. 10, 1985

[54] BREWING APPARATUS

[75] Inventor: Christopher J. L. Brown, Ipswich, England

[73] Assignee: Bowmans Brewer, Ltd., Suffolk, England

[21] Appl. No.: 624,288

[22] Filed: Jun. 25, 1984

[51] Int. Cl.[4] ................................................ C12C 9/00
[52] U.S. Cl. ........................................ 99/278; 426/16; 435/289
[58] Field of Search ....................... 99/276, 277, 277.1, 99/278; 426/16, 231; 435/289, 291, 302, 317

[56] References Cited

U.S. PATENT DOCUMENTS 2,948,617  8/1960  Paine ..................................... 99/278
3,201,328  8/1965  Williams ............................... 99/276
4,388,857  6/1983  Korek ................................... 99/278

Primary Examiner—Robert W. Jenkins
Attorney, Agent, or Firm—Larson and Taylor

[57] ABSTRACT

Brewing apparatus for batch brewing beer or ale comprises a fermentation vessel 1 in which a fermentable liquor is contained, a float hydrometer 11 and a sensor 12 for monitoring downward displacement of the hydrometer 11 as the specific gravity of the liquor reduces due to fermentation. The sensor 12 includes means for providing a signal in a controller 3 at a desired specific gravity to indicate completion of the required fermentation and the controller 3 is operable to control automatic transfer of the fermented liquor to a maturing vessel 4 and, after a predetermined time interval to a barrel or the like.

19 Claims, 6 Drawing Figures

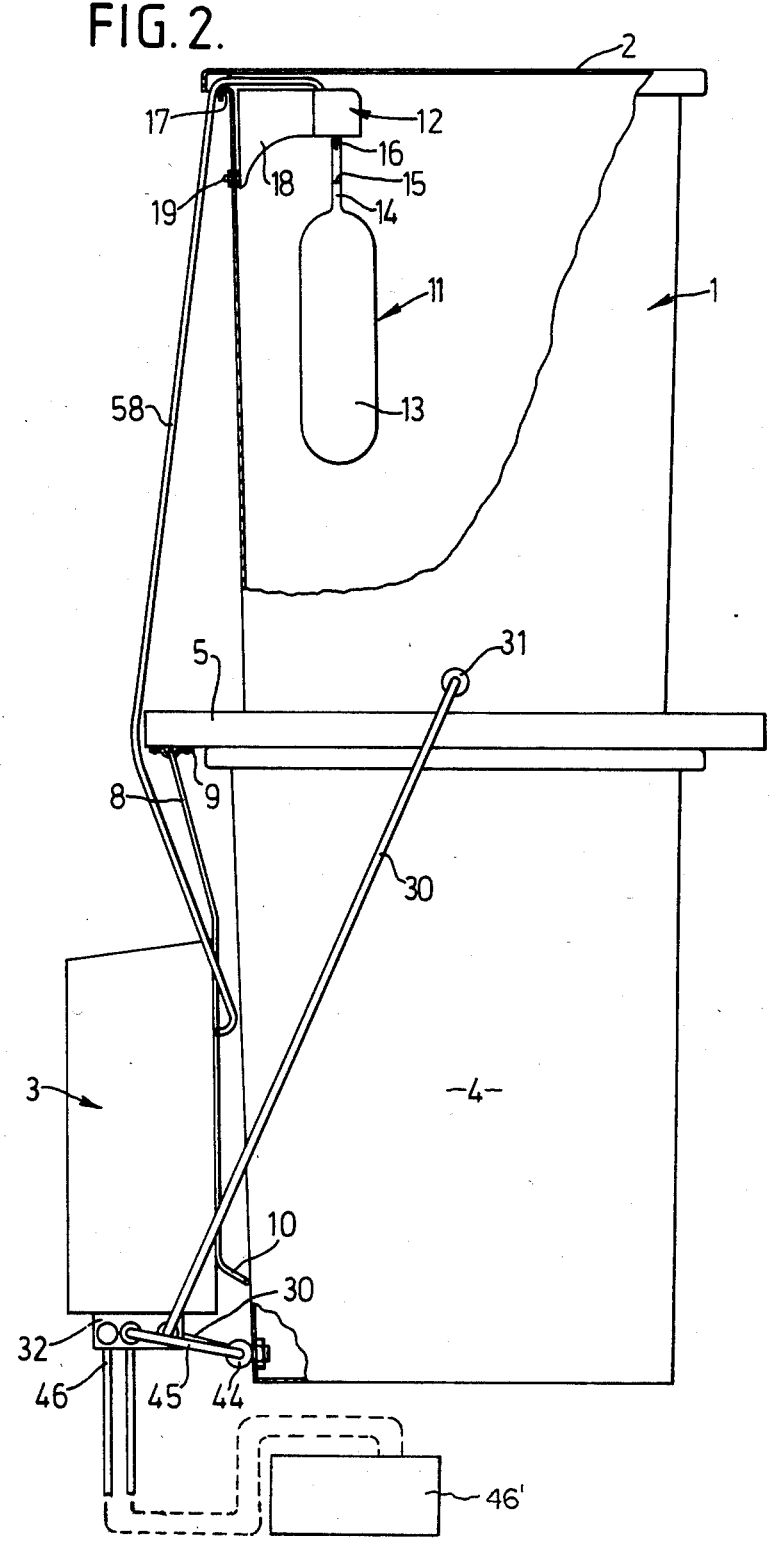

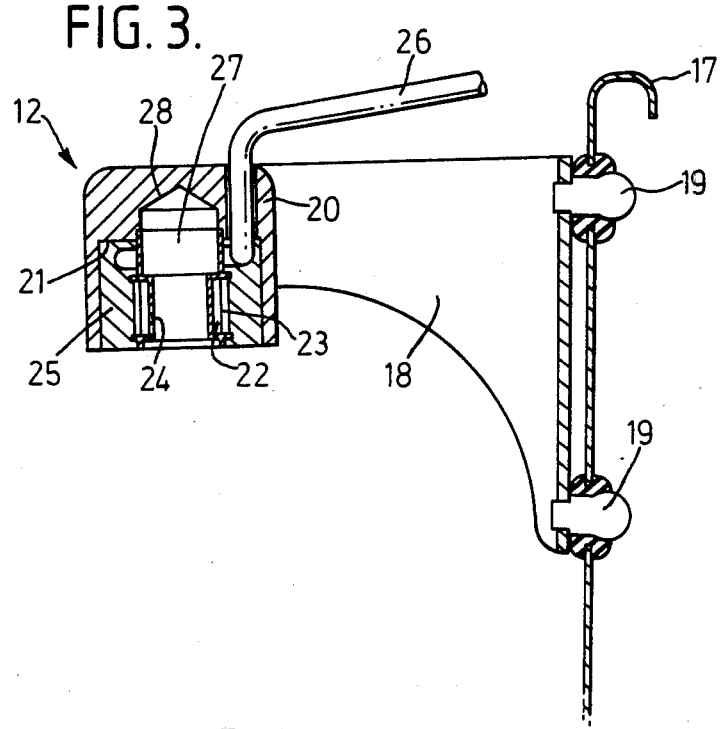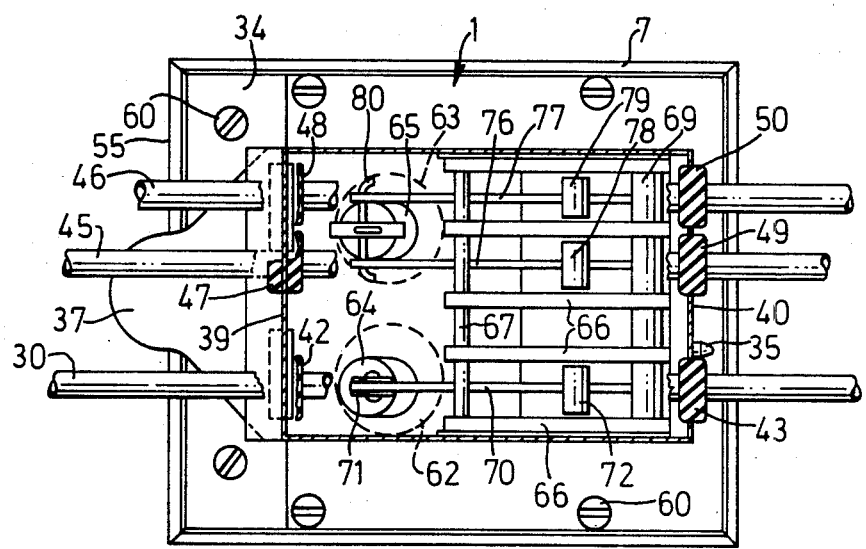

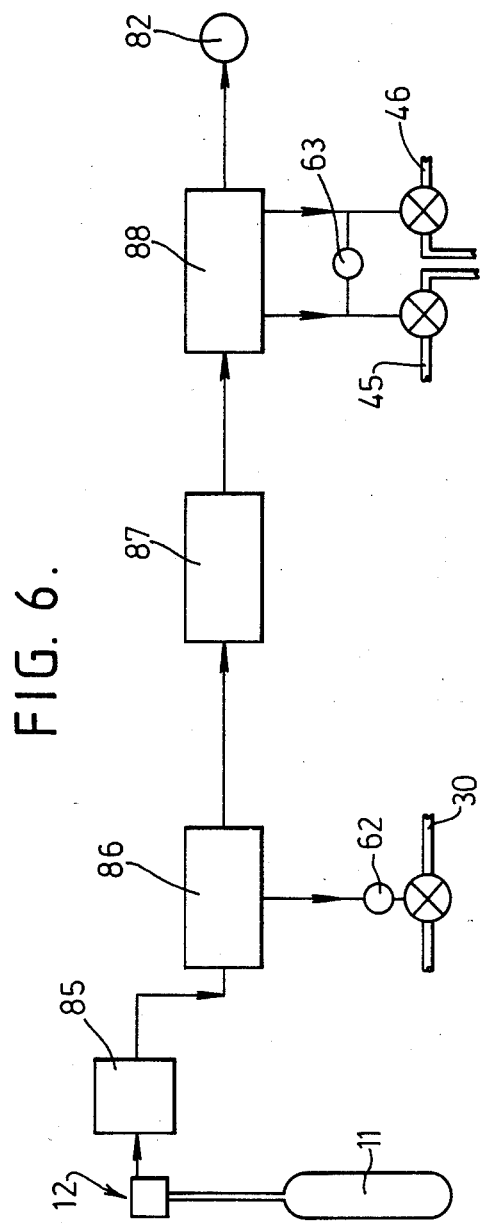

BREWING APPARATUS

BACKGROUND OF THE INVENTION

This invention concerns apparatus for brewing and has particular application in brewing relatively small batch quantities of beer or ale such as carried out for domestic consumption by an amateur brewer.

As will be understood, in the home brewing of beer one of the critical phases is that of fermentation of the wort and the racking of the wort at the proper stage when the fermentation is approaching completion. The rate of fermentation and the successful completion of same is dependent on many factors and, to the amateur brewer, some of these are exceedingly difficult to control to the degree essential for producing a quality beer. Important factors are the risk of contamination, the quantity and quality of the ingredients and preparation, the temperature and environmental situation or influences.

In practice, the amateur brewer usually prepares a batch quantity of about five Imperial gallons (22.73 liters) and the fermentation vessel is a suitable size container such as a plastics bucket or bin. The prepared wort is poured into such container and left for a period of time for fermentation to proceed. At the end of the period, the liquor must be racked, usually by siphoning from such container, and carefully transferred to another vessel without contamination or excessive contact with air.

The physical handling of the wort and liquor presents problems as well as the need for stringent hygiene and other requirements.

SUMMARY OF THE INVENTION

An object of this invention is to provide brewing apparatus for batch brewing beer or ale which overcomes certain of the problems such as above-mentioned, and by which the amateur brewer is assured that the wort is in a proper state for the maturing stage which will be followed by racking and the subsequent conditioning stage.

Further objects of other aspects of this invention include providing a fermentation vessel in combination with a second vessel and special controls by which the wort is automatically transferred from the fermentation vessel to the second vessel for maturing.

Other objects of further aspects of this invention include controlled and automatic transfer of the matured liquor for final conditioning.

According to the present invention there is provided brewing apparatus for batch brewing beer or ale wherein a fermentation vessel is arranged to contain a quantity of liquor, a float hydrometer has a stem receivable within a sensor mounted in the vessel and arranged to limit upward displacement of the hydrometer, the sensor including means responsive to downward displacement of the hydrometer stem, and a controller connected to the sensor, the arrangement being such that, in use, with the vessel filled with liquor having a high specific gravity, the stem of the hydrometer is received within the sensor and, as the specific gravity of the liquor reduces due to fermentation, the hydrometer stem is displaced downwardly from the sensor until, at a desired specific gravity, the sensor means responds to provide a signal in the controller for indicating the desired completion of fermentation.

By this invention, a float hydrometer is employed to maintain a constant monitor of the specific gravity of the liquor during fermentation. In known manner, the float hydrometer is calibrated for the specific gravity range for beer or ale, and as the desired correct specific gravity is reached during fermentation, the float will tend to sink causing downward displacement of the stem relative to the sensor. At a predetermined position the means in the sensor will respond to control the signal to be provided by the controller.

This relatively simple concept has the significant advantage of ensuring the amateur brewer knows exactly when the fermentation is at the required stage for racking and the monitoring is constant so that variations in fermentation rate do not affect the response.

The hydrometer is limited by the reception of the stem in the sensor so that displacement of the hydrometer is prevented and location of the hydrometer within the vessel is provided.

Preferably, in the fermentation vessel the stem of the hydrometer includes a body of ferro-magnetic material arranged to interrupt the resonance of one of two concentric coils in the sensor when the hydrometer stem is received within the sensor with the ferro-magnetic body aligned with the coils, and the controller includes means monitoring the resonant output so that on a change when the hydrometer is displaced downwardly, the signal is provided to the controller.

The arrangement for sensor response using two coils of which the resonance of one coil is interrupted by a body of ferro-magnetic material of the hydrometer stem is a reliable and simple system by which accurate monitoring of the resonant output can be achieved.

One coil having a lower number of turns is arranged to excite the resonance of the other coil having a higher number of turns. The exciter coil has a high frequency voltage applied to it, and the other coil is arranged to be resonate in excited response to the exciter coil. The inductance of the resonant coil is altered when the ferro-magnetic material is aligned therewithin and the resonance is interrupted. In one arrangement of the sensor, the resonant coil is located within the exciter coil.

The coils are encapsulated in the sensor body for safe mounting and the body of ferro-magnetic material, such as a mild steel slug, is also safely enclosed in the stem. When the hydrometer stem is displaced downwards on falling of the specific gravity, the ferro-magnetic body is carried away from the coils permitting the resonance to be restored.

Conveniently, in the monitoring of resonant output voltage by circuitry of the controller, a time delay can be introduced to ensure that erroneous responses caused by any bobbing of the hydrometer are overridden.

According to another preferred feature, the stem of the hydrometer has a reference mark to indicate the level to which the vessel is to be filled with the liquor, the sensor has a blind recess into which the free end of the stem is received, and the reference mark is at a position on the stem spaced a distance from the free end of the stem relative to the bottom wall of the recess so as to be visible when the stem is received and constrained in the blind recess.

By such preferred arrangement, the sensor which is mounted on the vessel wall defines the upper limit to which the hydrometer can float, and this is fixed relative to the vessel. The reference mark on the hydrometer stem denotes the level to which the vessel is to be filled, and provides a level directly associated with the sensor mounting. This is far better than relying on register marks on the wall of the vessel.

The hydrometer has to be calibrated in the normal manner for the range of specific gravities, and by selecting the distances or lengths between the free end of the stem, the position of the sensor responsive means relative to the blind end of the recess, it is possible to ensure that the hydrometer is supported to the upper limit when the fresh liquor is poured into the vessel.

Preferably, the hydrometer has a large volume bulb and a small diameter stem so that it gives a high sensitivity to the relatively small range of specific gravities applicable during the final stages of fermentation.

The hydrometer is not fixed or otherwise secured within the fermentation vessel, and can easily be removed or fitted manually in the sensor. This is of practical importance in the event of replacement. Furthermore, the sensor is preferably carried on a bracket or clip simply slung on the rim of the fermentation vessel so that it can also be removed or replaced easily.

As will be understood, on completion of fermentation as indicated by the controller, the liquor must be transferred to another vessel for maturing. The usual process is to siphon off the liquor into another vessel where, protected from free circulating air, it matures. This transfer is a tiresome and often tedious job for the amateur often leading to spoiling of the brew by contamination. Furthermore, the transfer should be done at the correct time for best results, and often this is not possible or feasible when the transfer has to be done manually.

According to another preferred feature of this invention, the fermentation vessel is connected to a second vessel by a tube and valve means is provided for controlling the flow of fermented liquor from the fermentation vessel to the second vessel. The valve means is actuated by the controller so that the fermented liquor is transferred on actuation of a valve mechanism by the controller following the response of the sensor to downward displacement of the hydrometer stem at the required degree of fermentation.

The fermentation vessel is connected to the second vessel but the connection through the tube is closed whilst fermentation proceeds. Only when the fermentation is at the right stage sensed by the sensor is the connection opened by the controller actuating the valve mechanism. Thus the transfer of the fermented liquor is done automatically at the desired stage without any handling by the brewer.

The controller is also preferably arranged to close the connection following the transfer of the fermented liquor.

In one construction of the apparatus, the transfer tube is of flexible and resilient material and the valve mechanism is arranged to apply pressure to the tube to close same by resiliently squeezing the tube flat, and on release of the pressure the tube opens by resilient restoration.

The valve mechanism may include a pivotal lever arranged to apply pressure to the transfer tube.

By such an arrangement there is no risk of contamination of the liquor by a valve body or stop cock through which the liquor has to flow, and there is little or no risk of blockages arising.

In another construction of the apparatus, the transfer tube may be connected to an electrically operated diaphragm valve having an inlet coupled to the transfer tube and an outlet which is opened on actuation of the valve.

According to yet another feature of this invention, the controller may include means for discharging the liquor from the second vessel in which the liquor has been allowed to mature for a required time interval.

Preferably, for such an arrangement the second vessel is connected to both a discharge tube and a relief tube and the controller includes a valve mechanism for controlling flow through said discharge and relief tubes with the valve mechanism being operable at a timed interval following transfer of the liquor to the second vessel.

On actuation of the valve mechanism, the matured liquor is discharged through the discharge tube and the relief tube is opened to atmosphere to vent the apparatus.

The discharge and relief tubes may each be flexible and resilient with the valve mechanism for these tubes being similar to that for the transfer tube. The three flexible and resilient tubes may extend across a flat base plate for respective pressure squeezing against the plate by the associated valve mechanisms to control the flow through the respective tubes.

Alternatively, the valve mechanism may comprise respective electrically operated diaphragm valves similar to that used for the transfer tube.

Various types of valves with appropriate mechanisms could be used to suit the apparatus being in mind the essential requirements of simplicity and no risk of line blockage.

The controller may include circuitry for actuating the valve mechanism or mechanisms as well as other devices such as timers.

Other features, objects and advantages of this invention in it's various aspects will be referred to later.

In order that this invention in its various aspects be understood, an exemplary batch brewing apparatus will now be described with reference to the accompanying drawings.

BRIEF DESCRIPTION OF THE DRAWINGS

FIG. 2 is a side elevation of the apparatus depicted in FIG. 1 with certain parts shown broken away;

FIG. 3 is an enlarged detail of part of the apparatus comprising a sensor in the fermentation vessel;

FIG. 5 is a partially sectioned view of the controller in the direction V—V shown in FIG. 4; and FIG. 6 is a block diagram relating to the function of the apparatus and the controller.

DETAILED DESCRIPTION OF THE EXEMPLARY EMBODIMENT

Figure 1:
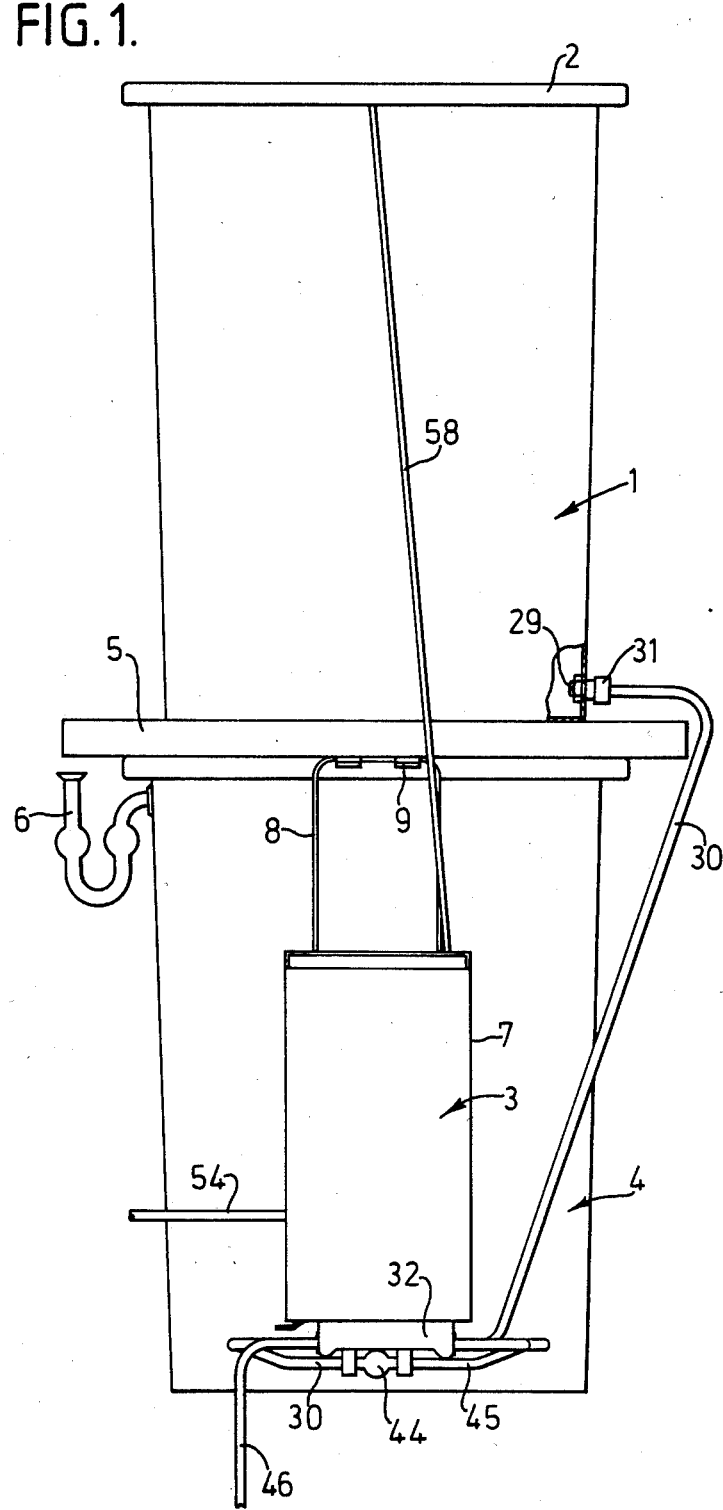
FIG. 1 is a front elevation of the apparatus.

With reference to the drawings, the apparatus comprises certain principal parts being an open topped fermentation vessel 1 and a lid 2 therefor, a controller 3 including certain valve means for transferring wort from the fermentation vessel 1 to a closed second vessel 4 with the valve means of the controller being operable to empty matured liquid from the vessel 4 for conditioning.

The fermentation vessel 1 and the second vessel 4 are each arranged to contain the same volume of liquid, for example about 5 Imperial gallons (22.73 liters), such volume being typical for home brewing of beer. The vessels are similar and are cylindrical with substantially flat bottoms and upright side walls. The vessels are made of suitable material, such as plastic or stainless steel, which will not taint the liquor and is corrosion resistant, capable of being sterilised and withstanding the conditions prevailing during brewing.

The second vessel 4 is arranged to stand on it's base or a plinth (not shown) with the fermentation vessel 1 supported vertically above on a flat circular divider board 5 of which the marginal edges project beyond the respective side walls of the vessels 1,4. The board 5 is set on the closure of the second vessel which is seated in an airtight manner on the top rim of the vessel. An airlock 6 is connected to the second vessel to permit exhaust of gasses in known manner.

The controller 3 is enclosed in a box-like housing 7 and is supported by a bracket 8 connected at it's upper end to the underside of the divider board 5 by a clip 9. The lower part of the bracket 8 is offset to provide a laterally displaced abutment end 10 engaging the side wall of the second vessel 4 and supporting the controller 3 in spaced relationship therefrom.

In the fermentation vessel 1 there is supported a hydrometer 11 and a sensor 12. The hydrometer 11 comprises a large bulb 13 and a small diameter stem 14 carrying a reference level mark 15. A slug 16 of ferromagnetic material such as mild steel is mounted in the stem 14 at a specified fixed distance from the free end which is arranged to be received in the sensor 12.

As best shown in FIG. 3, the sensor 12 is carried adjacent the rim 17 of the fermentation vessel 1 by a bracket plate 18 secured to the wall of the vessel by suitable fasteners 19. The sensor 12 comprises a squat cylindrical body 20 having a blind counterbore 21 in which first and second coils 22,23 respectively wound on a hollow common former 24 are mounted by potting compound 25. Each coil 22,23 is connected to a screened two core cable 26 entering the body 20 through a lead hole.

In the sensor 12, the coils 22,23 and wires are sealed and encapsulated by the potting compound 25 leaving a central blind recess 27 into which the end of the stem 14 is received. The coils 22,23 are wound coaxially and the coils 22,23 are spaced from the bottom wall 28 of the recess by a distance which corresponds to the distance between the free end of the stem 14 and the slug 16 so that when the hydrometer 11 is fitted with the stem 14 within the blind recess 27 to abut the bottom wall 28, the slug 16 is aligned within the concentric coils 22,23.

The fermentation vessel 1 has an outlet 29 adjacent the bottom into which one end of a transfer tube 30 is fitted by means of a gland fitting 31. The transfer tube 30 is of flexible and resilient material and extends downwardly to be located in a tube support plate 32. Mounted on the bottom of the controller housing 7 there is a frame 34 to one side flange of which the support plate 32 is mounted by a pair of pegs providing a releasable pivot 35. The frame 34 on the side opposed to the pivot 35 has a re-entrant flange portion 36 which provides a projection for engagement by a spring clip 37 integral with the support plate 32. The support plate 32 may be located in the upper position depicted in the drawings and held therein by the clip 37, and as desired, by releasing the spring clip 37 the support plate 32 may be lowered, and detached if required.

The support plate 32 is of substantially rectangular shape having upstanding walls of which the front wall 39 terminates in the spring clip 37, and the rear wall 40 includes the pivot mounting. The centre portion of the plate 32 provides a flat base 41 across which the transfer tube 30 lies being located through grommets 42,43 respectively seated in aligned opposed piercings in the front and rear walls 39,40 of the support plate 32.

The portion of the transfer tube 30 which lies across the flat base 41 is arranged to be squeezed flat to close the tube by a first valve mechanism to be described later. The transfer tube 30 terminates in one side of a gland fitting 44 located in an opening adjacent the bottom of the second vessel 4.

The other side of the gland fitting has connected thereto one end of a discharge tube 45 which extends through the support plate 32. A relief tube 46 also extends through the support plate 32 and one end is connected by a gland fitting (not shown) to the second vessel. The other ends of the discharge and relief tubes 45,46 remote from the support plate 32 are adapted in use to be coupled to a barrel 46'. The discharge and relief tubes 45,46 are also of a flexible and resilient material whereby they may respectively be squeezed flat to close them by a valve mechanism. The two tubes 45,46 extend closely parallel across the flat base 41 being located by respective grommets 47,48 in openings in the front wall 39 and grommets 49,50 in the rear wall 40. The associated valve mechanism is arranged to act in unison on the discharge and relief tubes 45,46.

The controller 3 comprises the housing 7 in which first and second circuit boards 51,52 are mounted by suitable fixings 53. Mains electricity is conducted to the first circuit board 51 by a cable 54 entering the housing 7 through an opening in the front side wall 55 of the housing 7. The top of the housing 7 comprises a cover plate 56 releasably secured to an internal top flange 57 by fasteners. The lead 26 from the sensor 12 extends into the housing 7.

The bottom of the housing 7 has an internal flange 59 to which the aforesaid frame 34 is secured by fasteners 60 as well as a bottom cover 61 of shaped profile. Inside the housing 7 there are two solenoids 62,63 each mounted on the bottom cover 61 aligned with apertures through which the respective plungers 64,65 extend towards the tube support plate 32. The solenoids 62 and 63 are connected to the circuitry for operation to retract or extend the respective plungers 64,65 as controlled by the circuit.

The electrical components may be shielded from the valve mechanism by a water-proof sheet within the housing, and the arrangement of the circuit boards may be varied. For instance, the components of both boards shown may be integrated into a single board.

The three tubes 30,45,56 extend across the flat base 41 between a set of spacer plates 66 that extend parallel to the tubes and are fixed together by a front cross pin 67 extending between two opposed drop plates 68 depending from the opposed sides of the frame 34. A spindle 69 extends through the other ends of the spacer plates 66 between the drop plates 68.

A valve lever 70 associated with solenoid 62 has one end pivotally mounted on the spindle 69 and extends between two spacer plates so as to overlie the extent of transfer tube 30. The other end of valve lever 70 is connected to the solenoid plunger 64 by a link 71 so that movement of the plunger 64 causes the lever 70 to rock on the spindle 69. The downward movement of the lever 70 is limited by the cross pin 67. Intermediate the ends of the valve lever 70 and on the underside there is mounted a transverse press bar 72 which is arranged to engage with the underlying transfer tube 30. One end of a spring 73 is located in a pocket 74 formed in the bottom cover and extends towards the aligned valve lever 70. A press foot 75 is mounted on the other end of the spring 73 and this engages the topside of the valve lever 70 aligned with the press bar 72.

By this arrangement of the solenoid 62 and the valve lever 70 and spring 73, the press bar 72 is pressed on the tube 30 to close same by squeezing it flat when the solenoid plunger 64 is extended. On retraction of the plunger 64, the valve lever 70 is lifted against the spring pressure and the tube 30 may restore to the open condition.

In a similar construction and manner, the other solenoid 63 controls two parallel valve levers 76,77 which are aligned respectively with the discharge and relief tubes 45,46. The levers 76 and 77 are each pivotally mounted at one end on the spindle 69 and carry respective transverse press bars 78,79. There are two springs with press feet (not shown) arranged to act on each valve lever 76,77 and the plunger 65 of solenoid 63 carries a cross link 80 to which each valve lever 76,77 is coupled.

Accordingly by the arrangement of solenoid 63 and associated valve levers 76,77 both the discharge and relief tubes 45,46 are maintained closed when the plunger 65 is extended, and on retraction of the plunger 65, both valve levers 76 and 77 are lifted to permit both the tubes to open.

It should now be noted that when the tube support plate 32 is lowered, then all the tubes carried by the plate are released from engagement with the respective valve levers so that all tubes may be simultaneously open. The downward movement of the valve levers is limited by the cross pin 67. When both solenoids 62,63 are extended with the valve levers depressed, on closing the tube support plate 32 to the housing 7, all tubes are closed simultaneously.

In order to understand the operation and function in use of the apparatus, further description of the controller control circuitry is required and reference will now be made also to the block diagram of FIG. 6. However, only a brief description of the function of the circuitry will be given as the specific components and wiring details are not considered essential to understand this exemplary embodiment of the invention.

The cover plate 56 of the housing 7 mounts an optional power on/off switch 81 to control the mains supply to a heater (not shown). There are various LED indicators 82, a power indicator 83, and various push switches 84.

In the housing 7, the controller components include a sensor circuit 85 associated with the sensor 12; a timer 86 for the transfer and associated with controlling solenoid 62; a timer 87 for maturing and a timer 88 for transfer for conditioning, these timers being associated with controlling solenoid 63. The timers are connected to respective ones of the LED indicators 82.

In the sensor circuit 85, a fixed frequency oscillator is arranged to excite the coil 22, and the other coil 23 is connected and arranged in the circuitry so that the coil 23 can resonate being excited by the other coil 22. The resonant output voltage is monitored. The resonance is interrupted when the slug 16 of the hydrometer stem 14 is inserted aligned with with coils for the inductance of the resonating coil is changed. Resonance only occurs when the slug 16 is displaced away from the coils 22,23.

By this resonance and the monitoring thereof, and the setting of the hydrometer, a control sensing the completion of fermentation can be applied. The control sensing produces a signal or like trigger to be employed for indicating such completion and, as required, to progress to the next stage of the control programme.

The timers are arranged for successive actuation to be operable and to initiate the control circuitry to actuate the solenoids to automatically operate the valve mechanisms.

Figure 4:
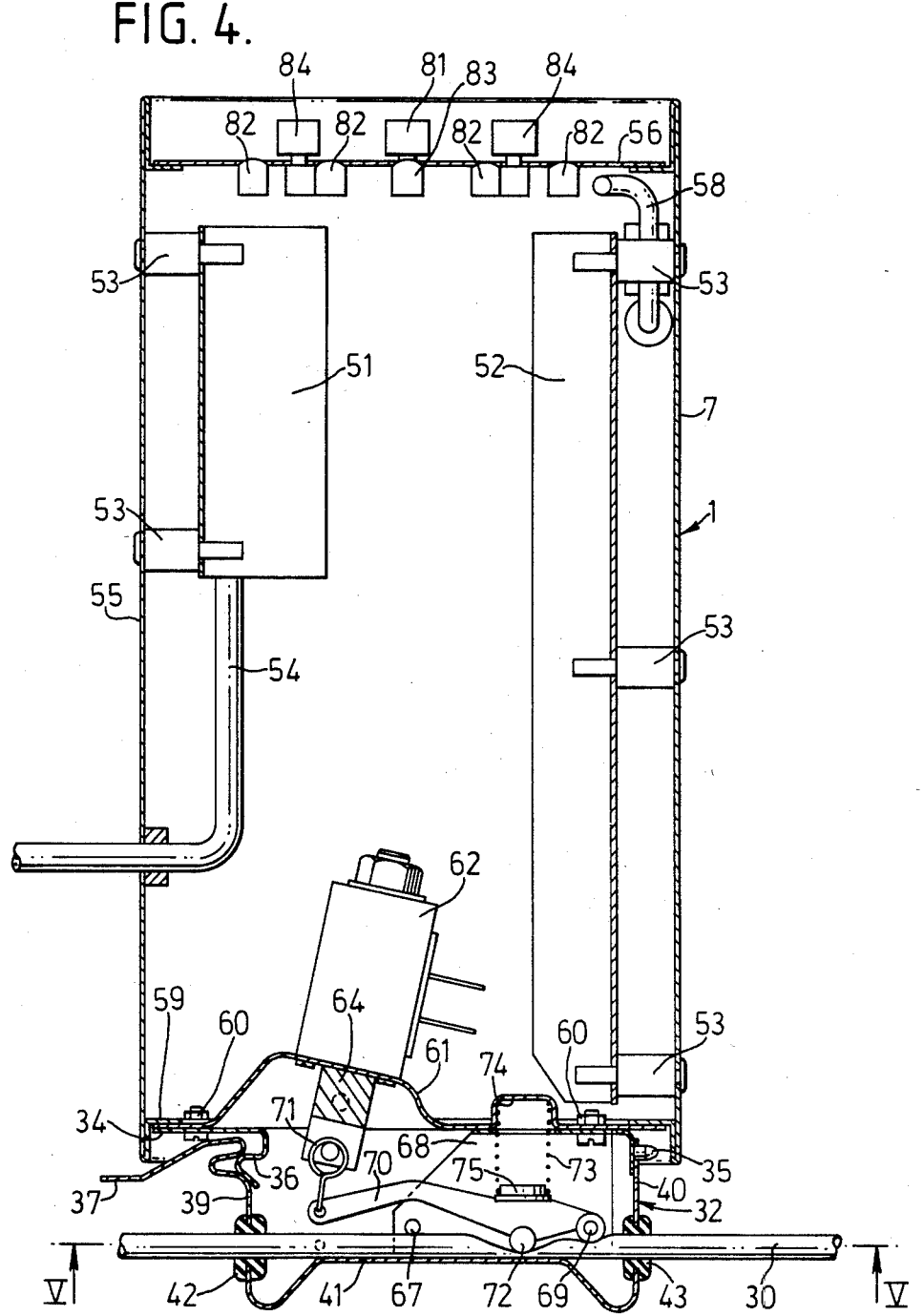
FIG. 4 is an enlarged vertical section of another part of the apparatus comprising a controller.

This will now be described with reference to use of the apparatus. It will be assumed that the apparatus is cleaned and the tubes connected as aforedescribed with all tubes closed by the valve mechanisms, that is as shown in FIGS. 4 and 5.

In the use of the apparatus, the prepared wort is prepared and poured into the fermentation vessel of the apparatus. To this the yeast and any other ingredients are added. The stem 14 of the hydrometer 11 is fitted into the recess 27 of the sensor 12, and the level of the liquor made up to coincide with the mark 15 on the stem 14. Due to the higher specific gravity of the wort (usually from 1.028 to 1.075) before fermentation, the hydrometer 11 will float high and the free end of the stem will engage the bottom wall 28 of the blind recess 27 limiting movement of the hydrometer.

Thus by ensuring that the level of the liquor is as prescribed and as marked on the hydrometer stem, the slug 16 is aligned with the concentric coils 22,23 of the sensor 12. The resonance of the two coils in the sensor 12 is interrupted or cannot arise whilst the hydrometer stem 14 is held up in the sensor.

The liquor is left to ferment after the lid has been fitted, and if desired a thermostatically controlled heater may be employed to maintain the required temperature.

As fermentation proceeds, the specific gravity of the liquor reduces until it approaches the desired value, usually from 1.006 to 1.000. At this stage, the hydrometer 11 starts to sink causing the stem with the slug 16 to be displaced downwards from the blind recess 27 of the sensor 12. Eventually, as the slug is displaced sufficiently at the required specific gravity value, the resonance of the coil occurs and the variation in the voltage provides a monitored signal to trip the circuit to the next stage.

As a safeguard, the circuit may include a time delay to preclude monitoring of any erroneous resonance change caused by 'bobbing' of the hydrometer in the liquor.

In the next stage, the solenoid 62 is actuated to withdraw the plunger 64 thereby lifting the valve lever 70 to release the pressure applied to the transfer tube 30 which had maintained it squeezed flat and closed. Accordingly, on opening the tube 30, the fermented liquor is transferred automatically by gravity flow from the fermentation vessel 1 to the second vessel 4. Any air in the second vessel 4 is displaced through the airlock 6.

When the circuit is tripped to this stage, the first timer 86 is started and it is on such starting that the initial signal is generated to actuate the solenoid 63. The transfer timer 86 times out after a period sufficient to complete the transfer of the liquor, and on timing out causes the release of the solenoid 63 to close the transfer tube 30 and simultaneously to initiate the start of the maturing timer 87.

The maturing timer 87 has a timer period of about six days, but this may be varied as desired to suit the type of beer or ale. When the timer 87 has timed out, a trip signal is generated to initiate the timer 88.

On starting timer 88, an initial signal is provided to actuate the solenoid 63 to displace it's plunger 65 so that the two valve levers 76,77 are lifted to open the discharge and relief tubes 45,46.

On such opening of the two tubes 45,46 the matured liquor is discharged directly into a suitable conditioning barrel or keg 46' and where a low pressure valved sealed barrel is used, the displaced air may be vented to atmosphere through the relief tube 46. The liquor is then to be left in the barrel for conditioning, and the timer 88 times out releasing the solenoid 63 to close the two tubes 45 and 46.

At this stage, the filled barrel is then isolated and depending on any valve or closure device fitted to the barrel may be disconnected from the apparatus. Of course, the liquor could be discharged into bottles for conditioning depending on the facilities or preference of the user.

In the operation of the apparatus, the LED indicators are arranged to indicate the functional stage or completion of same.

From the foregoing description of this exemplary embodiment, it will be appreciated that the comprehensive form of the apparatus provides an automatically controlled simple plant for batch brewing in which the control of successive stages including the transfer of the liquor is maintained following the completion of fermentation to the specified control specific gravity.

The apparatus is relatively simple as far as movable mechanical parts are concerned, and the operation of the valve mechanisms with squeeze flat tubes is readily appreciated by the amateur and non-technical person. Cleaning of all parts is no more difficult than with other forms of containers and contamination is avoided.

Although the apparatus is powered by mains supply, it could be arranged for battery operation. However, it is notable that with the controller above-described, in the event of mains power failure the solenoids will not be actuated to 'open' in the valve mechanisms. The arrangement of the solenoids is only to require power for holding off the valve levers.

Whilst the apparatus has deen described with the fermentation vessel connected to a second vessel with valve means for controlling the automatic transfer of the fermented liquor it will be understood that in its simplest form the apparatus comprises the fermentation vessel with the arrangement of the hydrometer and sensor by which the user may be given a signal that fermentation has been completed to the desired stage. The fermentation vessel may be provided as aforedescribed with a simplified form of controller omitting the valve mechanism and merely providing a visual or other indication when fermentation has been completed. The user may then use any suitable means to transfer the fermented liquor to a second vessel for maturing.

Such a fermentation vessel with a simple controller may form the basis of a kit of parts adapted to be purchased to construct the comprehensive apparatus as previously described.

The kit of parts may include a second vessel with a controller including a valve mechanism or mechanisms and one or more timers to indicate time for or control actuation of the valve mechanism(s).

The kit of parts may include a barrel for connection to the second vessel for direct discharge of the matured liquor to the barrel with the barrel having a one way pressure relief valve.

Although the foregoing preferred embodiment employs a sensor in which the desired specific gravity is monitored by the commencement of resonance, other types of sensor arrangements could be used to determine the movement of the hydrometer. For instance, other suitable sensors may include an optical system in which a portion of the hydrometer stem is opaque, and interferes with a receptor for an optic light beam so that on displacement of the opaque portion the receptor receives the light beam to generate a response; in another arrangement the sensor may include a capacitive detector.

Other forms of bracket support may be provided to permit removal of the housing from the vessels 1 and 4. Alternatively, the housing may be separate from the two vessels 1 and 4, and can be arranged to be free standing near the vessels with electrical leads and tubes extending thereto.

As far as the valve mechanism is concerned, other types of valves could be used such as diaphragm, poppet or disc valves. Furthermore, the valve mechanism could be actuated electrically by solenoids directly or indirectly by cams, latches or other typical mechanical means.

Various options or combinations are envisaged, and the inclusion of a thermostatic heater in the fermentation vessel with automatic cut-out on transfer of the liquor is a further option.

In a further embodiment of this invention, not shown in the drawings, many of the optional variations for the apparatus as aforementioned are incorporated. Briefly, the valve mechanism for controlling the flow of the fermented liquor for transfer for maturing comprises a direct acting electrically operated diaphragm valve such as typically used for low pressure applications in liquid flow lines with a solenoid actuating displacement of the diaphragm to open a valve port. The diaphragm valve has an inlet coupled to the transfer tube and an outlet which is opened on actuation of the valve. The outlet is connected by a tube to the maturing vessel. As aforedescribed, the solenoid of the diaphragm valve is operated by the circuitry of the controller in response to the monitored signal of the sensor of the float hydrometer.

By this valve mechanism the use of a pinch or squeeze flat tube is avoided, and this means that large bore more rigid tube or pipe can be employed reducing any risk of accidental pinching of the tube.

Additionally, similar diaphragm valves can be employed for the control of the flow through the discharge and relief tubes. Where three similar diaphragm valves are employed, these may be mounted in the housing with the respective inlet and outlets extending outwardly for connection to the respective tubes or pipes.

The automatic timer for the maturing stage may be omitted in a simplified form of the apparatus with the user being required to time the long interval for maturing. The controller circuitry may be integrated further with the omission of certain LED indicators. The controller may include a sequence stopper to permit the user to over-ride the automatic timing to reset the cycle.

Other variations may be incorporated within the broadest principle of this invention which is to provide the simplest form of apparatus with the controlled monitoring of the fermentation.

I claim:

1. Brewing apparatus for batch brewing beer or ale wherein a fermentation vessel is arranged to contain a quantity of liquor, a float hydrometer has a stem receivable within a sensor mounted in the vessel and arranged to limit upward displacement of said hydrometer, said sensor including means responsive to downward displacement of said hydrometer stem, and a controller connected to said sensor, the arrangement being such that, in use, with said vessel filled with liquor having a high specific gravity, said stem of said hydrometer is received within said sensor and, as the specific gravity of the liquor reduces due to fermentation, said hydrometer stem is displaced downwardly from said sensor until, at a desired specific gravity, said sensor means responds to provide a signal in said controller for indicating the desired completion of fermentation.

2. Apparatus according to claim 1 wherein said sensor means comprises two concentric coils and said stem of said hydrometer includes a body of ferro-magnetic material arranged to interrupt the resonance of one of said coils when said hydrometer stem is received within said sensor with said ferro-magnetic body aligned with said coils, and said controller includes means monitoring the resonant output so that on a change when said hydrometer is displaced downwardly, said signal is provided to said controller.

3. Apparatus according to claim 2 wherein said controller includes a time delay whereby erroneous resonance changes caused by bobbing or random movement of said hydrometer are overridden.

4. Apparatus according to claim 1 wherein said stem of said hydrometer has a reference mark to indicate the level to which said vessel is to be filled with the liquor, said sensor has a blind recess into which the free end of said stem is received and said reference mark is at a position on said stem spaced a distance from said free end of said stem relative to the bottom wall of said recess so as to be visible when said stem is received and constrained in said blind recess.

5. Apparatus according to claim 1 wherein said fermentation vessel is connected to a second vessel by a transfer tube and valve means is provided for controlling the flow of fermented liquor through said transfer tube.

6. Apparatus according to claim 5 wherein said valve means is actuated by said controller to permit transfer of fermented liquor from said fermentation vessel to said second vessel following the response of said sensor to downward displacement of said hydrometer stem to said desired specific gravity.

7. Apparatus according to claim 5 wherein said transfer tube is of flexible and resilient material and said valve means includes a valve mechanism arranged to apply pressure to said tube to close same by resiliently squeezing said tube flat, and on release of said pressure said tube opens by resilient restoration.

8. Apparatus according to claim 7 wherein said valve mechanism includes a spring loaded pivotal lever carrying a press bar arranged to engage said transfer tube, and said controller includes a first solenoid operable to pivot said lever against said spring bias to permit said transfer tube to open.

9. Apparatus according to claim 5 wherein said valve means comprises a diaphragm valve.

10. Apparatus according to claim 5 wherein said controller includes timer means operable to time out and initiate actuation of said valve means to transfer fermented liquor from said fermentation vessel to said second vessel.

11. Apparatus according to claim 5 wherein said second vessel is connected to a discharge tube and a relief tube and, second valve means is provided for controlling the flow of liquor through said discharge tube and for controlling the flow of air through said relief tube.

12. Apparatus according to claim 11 wherein said discharge and relief tubes are each flexible and resilient and said second valve means includes a valve mechanism arranged to apply pressure to said tubes to close same by resiliently squeezing said tubes flat, and on release of said pressure said tubes open by resilient restoration.

13. Apparatus according to claim 12 wherein said valve mechanism of said second valve means includes a pair of spring loaded pivotal levers, each lever carrying an associated press bar arranged to engage a respective one of said discharge and relief tubes, and said controller includes a second solenoid operable to pivot said levers against said associated spring bias to permit said tubes to open.

14. Apparatus according to claim 11 wherein said second valve means comprises a pair of diaphragm valves, each valve being coupled to a respective one of said discharge and relief tubes.

15. Apparatus according to claim 11 wherein said second valve means is operable to open/close said transfer and relief tubes in unison.

16. Apparatus according to claim 11 wherein said second valve means is operable by said controller at a timed interval following transfer of fermented liquor to said second vessel.

17. Apparatus according to claim 16 wherein said controller includes timer means operable to time out and initiate actuation of said second valve means.

18. Apparatus according to claim 11 wherein said discharge and relief tubes are connected to a barrel.

19. Apparatus according to claim 5 wherein said fermentation vessel is supported above said second vessel.

* * * * *